US007742933B1

(12) United States Patent
Royds

(10) Patent No.: US 7,742,933 B1
(45) Date of Patent: Jun. 22, 2010

(54) METHOD AND SYSTEM FOR MAINTAINING HIPAA PATIENT PRIVACY REQUIREMENTS DURING AUDITING OF ELECTRONIC PATIENT MEDICAL RECORDS

(75) Inventor: Robert B. Royds, Plainsboro, NJ (US)

(73) Assignee: Harrogate Holdings, Hamilton (BM)

( * ) Notice: Subject to any disclaimer, the term of this patent is extended or adjusted under 35 U.S.C. 154(b) by 0 days.

(21) Appl. No.: 12/383,445

(22) Filed: Mar. 24, 2009

(51) Int. Cl.
G06F 19/00 (2006.01)

(52) U.S. Cl. .......................................................... 705/3

(58) Field of Classification Search ...................... 705/2, 705/3, 4; 707/3; 704/9
See application file for complete search history.

(56) References Cited

U.S. PATENT DOCUMENTS

| 5,664,109 | A | 9/1997 | Johnson et al. ................. 705/2 |
| 6,182,029 | B1* | 1/2001 | Friedman ........................ 704/9 |
| 6,551,243 | B2 | 4/2003 | Bocionek et al. ............ 600/300 |
| 6,820,235 | B1 | 11/2004 | Bleicher et al. .......... 715/501.1 |
| 6,925,599 | B2 | 8/2005 | Wood .......................... 715/513 |
| 7,031,962 | B2 | 4/2006 | Moses ........................... 707/9 |
| 7,039,878 | B2 | 5/2006 | Auer et al. .................. 715/810 |
| 7,089,247 | B2 | 8/2006 | Kloos et al. .................... 707/10 |
| 7,165,221 | B2 | 1/2007 | Monteleone et al. ........ 715/738 |
| 7,187,790 | B2 | 3/2007 | Sabol et al. ................. 382/128 |
| 7,230,529 | B2 | 6/2007 | Ketcherside, Jr. et al. ...................... 340/539.12 |
| 7,284,196 | B2 | 10/2007 | Skeen et al. ................. 715/523 |
| 7,343,385 | B2 | 3/2008 | Lusen et al. ............. 707/104.1 |
| 7,415,447 | B2 | 8/2008 | Shiffman et al. .............. 706/47 |
| 2003/0140043 | A1 | 7/2003 | Hotchkiss et al. ............. 707/10 |
| 2004/0093240 | A1* | 5/2004 | Shah .............................. 705/2 |
| 2005/0149852 | A1 | 7/2005 | Bleicher et al. .......... 715/501.1 |
| 2005/0251011 | A1 | 11/2005 | Zahlmann et al. ........... 600/407 |
| 2005/0267782 | A1* | 12/2005 | Zahlmann et al. ............... 705/3 |
| 2007/0027722 | A1 | 2/2007 | Hasan et al. .................... 705/3 |
| 2007/0067189 | A1* | 3/2007 | Boris et al. ..................... 705/3 |
| 2007/0118399 | A1 | 5/2007 | Avinash et al. ................. 705/2 |
| 2007/0143273 | A1 | 6/2007 | Knaus et al. ................... 707/3 |
| 2007/0168331 | A1* | 7/2007 | Reddy et al. ................... 707/3 |
| 2007/0203746 | A1 | 8/2007 | DeHaan et al. ................. 705/2 |

(Continued)

Primary Examiner—Gerald J. O'Connor
Assistant Examiner—John A Pauls
(74) Attorney, Agent, or Firm—Watov & Kipnes, P.C.; Kenneth Watov

(57) ABSTRACT

A method and system for permitting a government agency or a medical research Institution to retain an independent Audit Agency to periodically audit a clinical trial testing the effect of experimental drugs on patients, being conducted by the Institution, to insure the audit conducted is in compliance with the privacy requirements of HIPAA. Prior to the audit, the Institution assembles individual electronic patient records relative to the clinical trial into an XML file in a discrete database, wherein each patient record has all personal information deleted, and such record is identified by a unique number or code assigned by the Institution. In turn, remote from the Institution, the Audit Agency transforms an appropriate search and indexing engine by adding to it libraries of text names, and synonyms, and constructs application programs containing the associated Protocol requirements and rules. The Audit Agency sends the transformed Search Engine to the Institution via the Internet or on CD's. The Institution runs the Search Engine against their database to produce a Compliance Report detailing all discrepancies found relative the Protocol course of medical treatment for each patient in the clinical trial, and sends the report to the Audit Agency. The Audit Agency processes the report to provide an Audit Report to Institution requesting comments, and if necessary, a corrective action plan.

23 Claims, 8 Drawing Sheets

U.S. PATENT DOCUMENTS

2008/0059241 A1 3/2008 Zahlmann et al. ............... 705/3
2008/0256128 A1 10/2008 Pierce et al. ............. 707/104.1
2008/0270181 A1 10/2008 Rosenberg .................... 705/2

* cited by examiner

METHOD AND SYSTEM FOR MAINTAINING HIPAA PATIENT PRIVACY REQUIREMENTS DURING AUDITING OF ELECTRONIC PATIENT MEDICAL RECORDS

FIELD OF THE INVENTION

The present invention relates generally to methods and systems for auditing electronic patient Medical Records, such as those stored in a computer memory, and more particularly to quality assurance auditing systems for clinical trials in the testing of potentially new drugs.

BACKGROUND OF THE INVENTION

Under the Health Insurance Portability and Accountability Act (HIPAA), health care organizations such as hospitals, drug testing Institutions, for example, must insure HIPAA compliance by protecting the confidentiality of patients' Medical Records. Audit Agencies involved in auditing patient Medical Records of health care organizations must be qualified in order to perform such audits, and the health organization or Institution must insure that the auditors do not breach the privacy of patients relative to their associated Medical Records. HIPAA requirements severely restrict the capability of health care organizations or Institutions to allow access to individual patient records. Such records are typically stored in large computer memories, and the records may include a large number of patients' Medical Records, or clinical research records, for example, whereby the associated healthcare organization must insure the privacy of such patients' records. Accordingly, any review of such records by an outside service group, such as an Auditing Agency must be from records that are free of the private information of each patient, such as their names, addresses, and so forth.

Healthcare organizations are Institutions ranging from the very small to the very large, and even individual practices, such as a sole practitioner physician, are increasingly implementing electronic Medical Record systems. A variety of database management systems are used to support this capability. Perhaps the most popular, underlying engine is Oracle®, but there are others such as Focus®. Many of the popular database programs have the capability to create database "dumps." There is a considerable range of choices in the way these dumps can be structured. The capability to output in a standardized "Markup" language is common with Extensible Markup Language (XML) being the currently preferred method. The electronic Medical Record itself and also the electronic clinical research record have defined structures in order to capture laboratory, special investigation, drug administration and medical/nursing progress notes in a structured format. Search Engines, typically, cannot search within databases and cannot index within. Creating a dump in a standardized "Markup" language creates a situation where a Search Engine can index and subsequently search the dumped data.

In order to obtain Federal Drug Administration (FDA) Approval for new drugs, drug companies must conduct clinical trials in accordance with a specific Protocol representing a plan for a course of medical treatment having a precise step-by-step description of the treatment plan associated with the experimental drug. Under FDA rules, clinical trials for a new drug particularly must pass through what are known as Phase 1, 2, and 3 Trials. The Phase 1 Trials are the earliest trials in the testing of a new drug, and usually involve up to about 30 patients. Phase 1 trials involve clinical or laboratory testing to show that a new treatment might help treat patients having a particular disease. The Phase 1 Trials are conducted to determine relative to the experimental drug, the safe dose range, side effects, how the body copes with the drug, and whether the treatment appears to treat the involved disease. Initially, the first patient to take part in the clinical study will be given a very small dose of the drug. If all goes well, the next person will get a slightly higher dose. With each patient taking part, the dose will gradually be increased, and the effect of each dose must be monitored, with any side effects being recorded. Blood tests and other monitoring will be conducted in order to determine how the drug is affecting the patients involved in the trial, how their bodies cope with the experimental drug, and how their bodies rid themselves of the drug after the dosages are stopped. Many times, people entering Phase 1 trials are healthy individuals, whereby the purpose of the trial is to monitor different dosage levels and side effects, in addition to pharmacodynamics and pharmacokinetics of the drug (how the body metabolizes the drug and how the drug affects the body). Testing is the first to be pursued before the drug can be tested as a potential new treatment for a particular disease to determine the efficacy of the new drug.

Phase 2 Trials are the next to be performed in testing a new drug. Only about 70% of potential new drugs proceed from Phase 1 Trials to Phase 2 Trials. The Phase 2 Trials are typically conducted on patients who all have the same type of disease, or with different types of a particular disease. Phase 2 Trials are conducted to determine whether a new treatment works well enough to pass on to Phase 3 Trials; the types of disease the drug appears to be effective against; increased information pertaining to side effects and how to manage them; and a determination of the most effective doses to utilize. The Phase 2 Trials may involve up to about 50 patients. If the Phase 2 Trial results indicate that prescribed new treatment is as good or better than an existing treatment, the drug will then be moved into Phase 3 Trials.

Phase 3 trials are conducted to measure results obtained with treatment utilizing the newer experimental drug when compared to the best currently available drug/treatment (standard treatment). It should be noted that the clinical studies involving Phases 1 through 3 may also involve other than new drugs, for example, radiotherapy treatments, X-ray or radiation treatments, and so forth. Phase 3 trials usually involve a much larger group of patients, perhaps thousands of patients in many different hospitals and even different countries, in view of the fact that differences in success rates may be small. Accordingly, the results obtained from many patients must be compared in order to show the difference between the treatment with the new drug and the standard drug.

The testing of a new drug, in any of the Phases, requires the maintenance of increasingly larger databases for typically accumulating in a computer memory the testing history for each patient in accordance with the Protocol. The FDA requires that the testing Institution, such as a hospital having a medical research center, work with an outside Audit Agency to insure that the established Protocol for any phase of the drug testing is being complied with. As previously indicated, the research center, hospital, or medical Institution must comply with HIPAA requirements that the privacy be protected for each patient involved in the various drug testing phases. As a result, any access given to personnel of an Audit Agency to the Medical Record system or patient database must have each patient's testing record kept intact while eliminating any information that might permit an auditor to identify the patient.

SUMMARY OF THE INVENTION

An object of the invention is to provide an auditing method and system that permits medical research hospitals or Institutions to comply with HIPAA privacy requirements relative to individual patient records maintained in a database involving the clinical testing of new drugs.

Another object of the invention is to eliminate the requirement that an Audit Agency send its personnel on site to a particular Institution in order to audit the Institution's database for patients specifically enrolled in clinical testing of a new drug in accordance with a particular Protocol.

Another object of the invention is to permit an Audit Agency to provide a Search Engine to Institutions conducting testing of new drugs, permit the Institution to have its own personnel run the Search Engine against the electronic patient records or database being maintained for the testing of a new drug.

With these and other objects of the invention in mind, relative to the problems in the prior art for auditing Medical Records involved in drug testing while maintaining the privacy of the patients as required by HIPAA, the present invention provides for an Audit Agency to transform a Search Engine for delivery to an Institution or medical research center involved in the testing of a new drug. The Institution is required to assemble individual computerized patient records obtained from clinical testing of a new drug, remove any information from each patient's record that might permit actual identification of the patient, and to assign for each patient record a unique number or code that is void of any private information regarding the patient. The records are stored in a computer memory in a database that permits the Institution to run the transformed Search Engine against the database to screen the patient records, and provide a Compliance Report that details any discrepancies uncovered in association with a given patient record or records relative to the Protocol established for conducting clinical tests. The Institution then delivers the Compliance Report to the Audit Agency. The Audit Agency processes the Compliance Report, generates an Audit Report that is sent to the Institution requesting particular comments, and if necessary, a corrective action plan from the Institution. As a result, the Audit Agency does not have any access to the identity of any of the patients involved in the clinical testing being audited.

BRIEF DESCRIPTION OF THE DRAWINGS

Various embodiments of the present invention are described below in detail with reference to the following drawings, in which like items may be indicated by the same reference designations, wherein.

DETAILED DESCRIPTION OF THE PREFERRED EMBODIMENTS OF THE INVENTION

Figure 1:
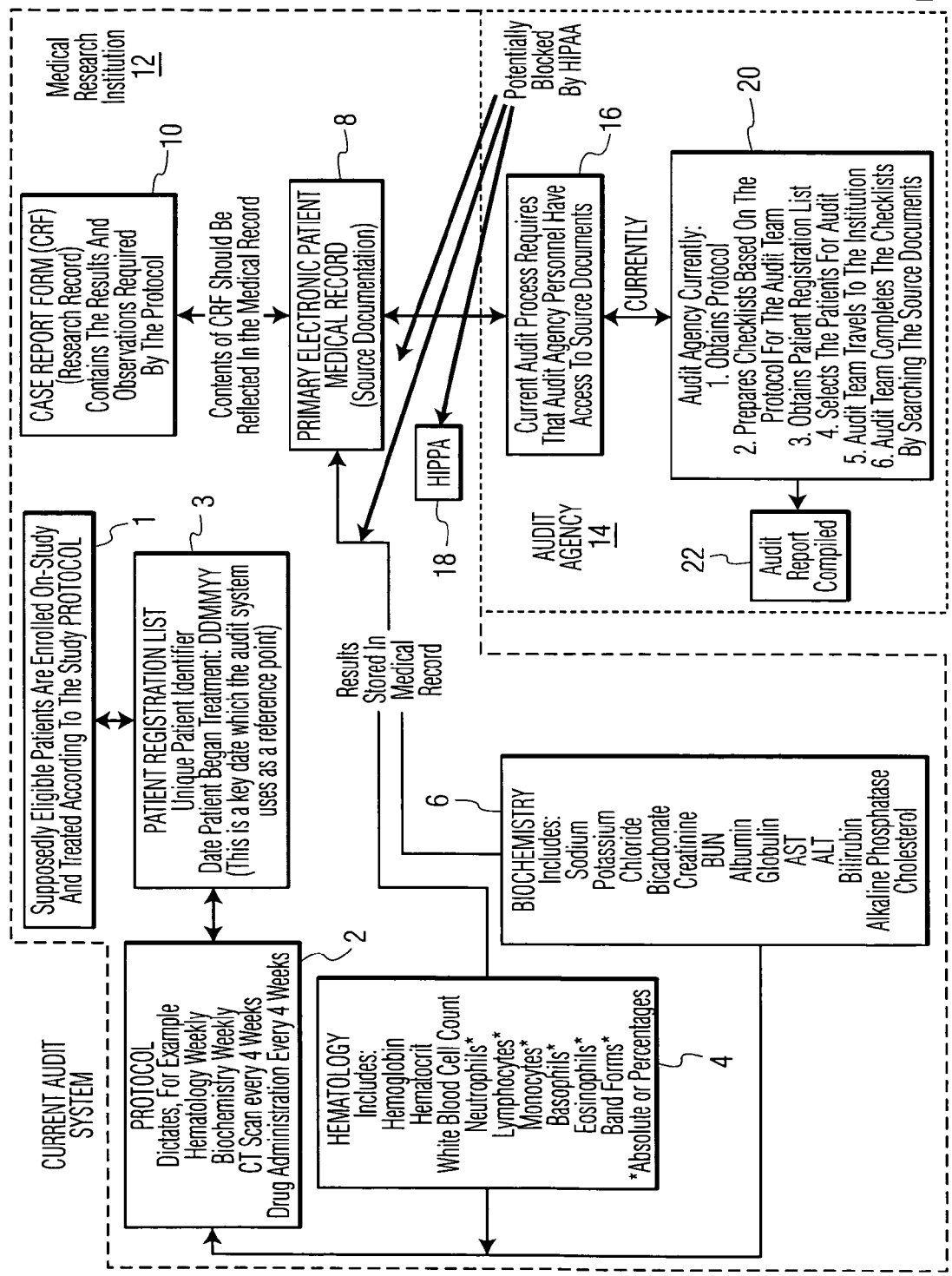
FIG. 1 is a flowchart showing a current audit system and method of the prior art.

As shown in the flowchart of FIG. 1, an example of a current audit system is shown. The first step 1 for the research hospital or Institution running the clinical study for a new drug is to enroll eligible patients for the study who are to be treated in accordance with a predetermined Protocol for the particular clinical trial. From this enrollment, a Patient Registration List is prepared with a unique patient identifier for each patient. As shown, all of the aforesaid are performed by the cognizant Medical Research Institution 12. An outside Audit Agency 14 typically employed to conduct an audit of the Primary Electronic Patient Medical Record Database 8 ensures that the Protocol 2 has been followed for each patient involved in the clinical trial or study. As further shown, Audit Agency personnel 16 must have direct access to the source documents in the patient Medical Record database 8. However, HIPAA privacy requirements 18 may potentially block access to these records by the Audit Agency personnel 16. If not blocked, the Audit Agency carries out auditing steps as indicated in block 20. Once the audit procedure 20 is completed, the Audit Agency 14 proceeds to compile an Audit Report 22. However, as indicated, due to recent privacy requirements now required by HIPAA, the medical research Institution 12 may be forced to block any access to the patient Medical Record database 8 by the Audit Agency personnel 16. Accordingly, there is an urgent present need in the prior art to provide an audit method which allows a detailed review of the patient Medical Record database 8 without interfering with a medical research Institution 12 HIPAA privacy requirements. To counter such requirements, external audit programs previously utilized by auditing agencies 14 are now blocked by HIPAA. The flowchart shows an example of a typical Protocol 2 for the scheduling of various tests as indicated. An example of the blood components tested for in the Hematology 4 is shown, along with an example of components to be included in Biochemistry Test 6. The Hematology 4 and Biochemistry 6 test results are stored in a primary electronic patient Medical Record database 8 including the test results for each patient involved in the particular phase of clinical testing of a particular drug. The research hospital or other Institution runs the clinical trial for the particular drug, and typically prepares a Case Report Form (CRF) 10 as shown, that is extracted from the patient Medical Record database 8.

Figure 2:
FIG. 2 is a flowchart for showing typical Protocol criteria in association with the Medical Record of a patient involved in a clinical testing of a drug, and the data that is typically extracted relative to the patient's Medical Record and the Protocol during the clinical testing.

In FIG. 2, a block diagram is shown for detailing the contents of a typical Protocol 2, patient Medical Record 24, and the Extracted Data 26 from a Medical Record 24 for inclusion in a Case Report Form 10. Accordingly, Protocol 2 dictates which data items are recorded on a Case Report Form 10, and the Medical Record 24 contains all of the source documentation from which the Case Report Form 10 is constructed via the Extracted Data 26.

Figure 3:
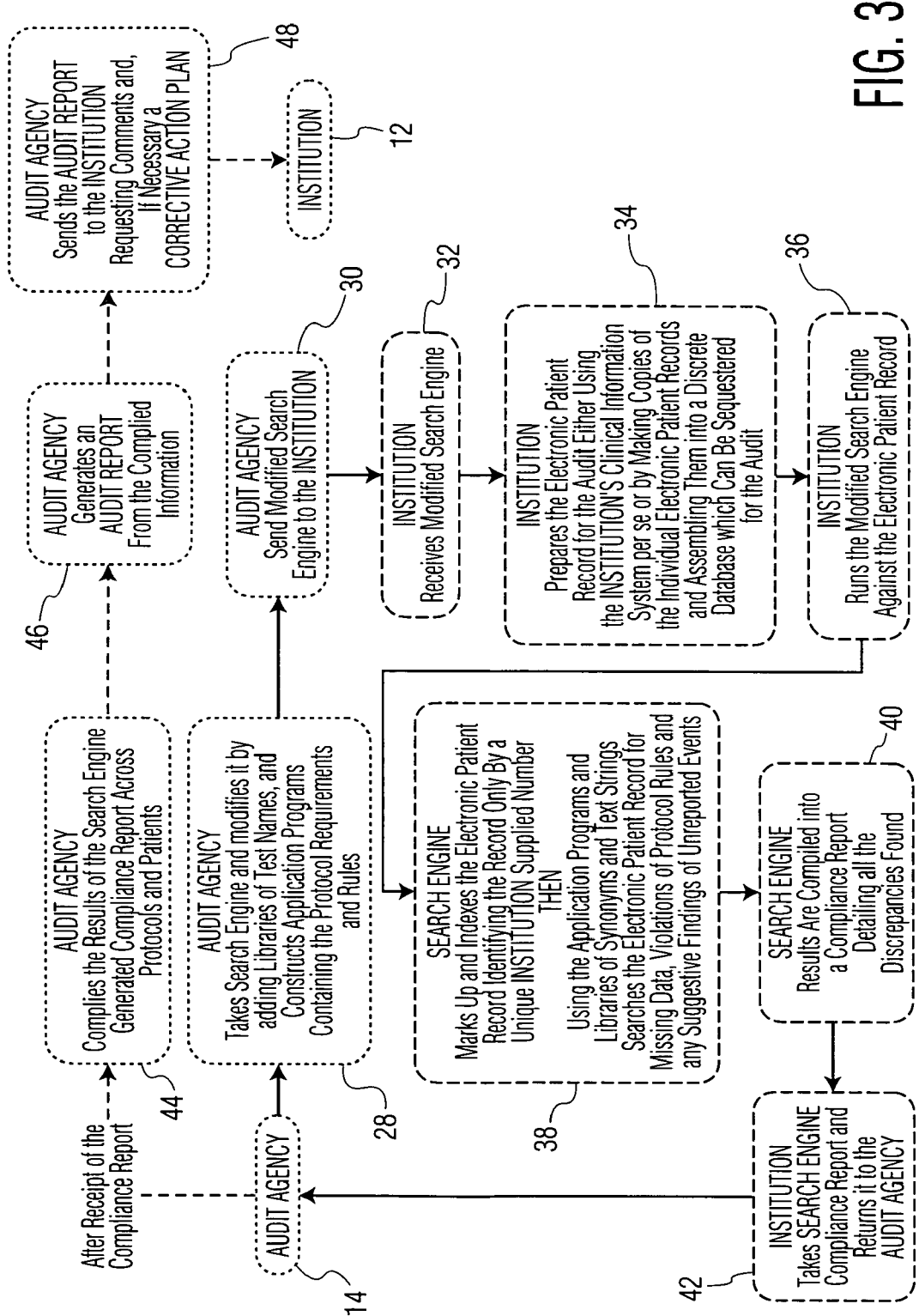
FIG. 3 is a flowchart showing the system and methodology for one embodiment of the present invention.

In FIG. 3, a flowchart is shown of a preferred embodiment of the method and system of the present invention. As shown, an Audit Agency 14 first transforms or builds a Search Engine as shown in Step 28, and then in Step 30 sends transformed Search Engine 28 either over the Internet or on a computer disk to a medical research Institution 12. In step 32, the Institution 12 receives the transformed Search Engine and proceeds to step 34 by preparing an electronic patient record database from clinical information or other individual patient records, in a manner excluding all private or personal identification of the patients, to prevent identification of the patients, thereby insuring personnel of the Audit Agency 14 cannot personally identify each actual patient involved in the study. Each patient's related information in the database will be identified by some unique code associated with that patient, whereby the Institution 12 will maintain the actual patient identification relative to the coding. In step 36, the Institution 12 employs its own personnel to run the transformed Search Engine 28 received from the Audit Agency 14 against the electronic patient record database assembled for the purpose of audit. Accordingly, the Audit Agency 14 has no direct involvement with the electronic patient records database assembled by the Institution 12. As shown in step 38, the Search Engine operates by performing the sub-steps indicated within step 38. In step 40, an Institution 12 further utilizes the Search Engine 28 to compile the search results into a Compliance Report that details all of the discrepancies found in noncompliance to the predetermined Protocol 2. In step 42, the Institution 12 sends the Compliance Report to the Audit Agency 14, by known communication means, such as the Internet, direct telephone transfer, or by delivering a computer disk or multiple computer disks containing the Compliance Report. Upon receipt of the Compliance Report, the Audit Agency 14, proceeds to step 44 to compile the Compliance Report results across Protocols and patients to in step 46 generate an Audit Report. Next, in step 48, the Audit Agency 14 sends the Audit Report to the Institution 12, wherein the Report includes a request for comments, and if deemed necessary, a request for a corrective action plan by the Institution 12.

Figure 4:
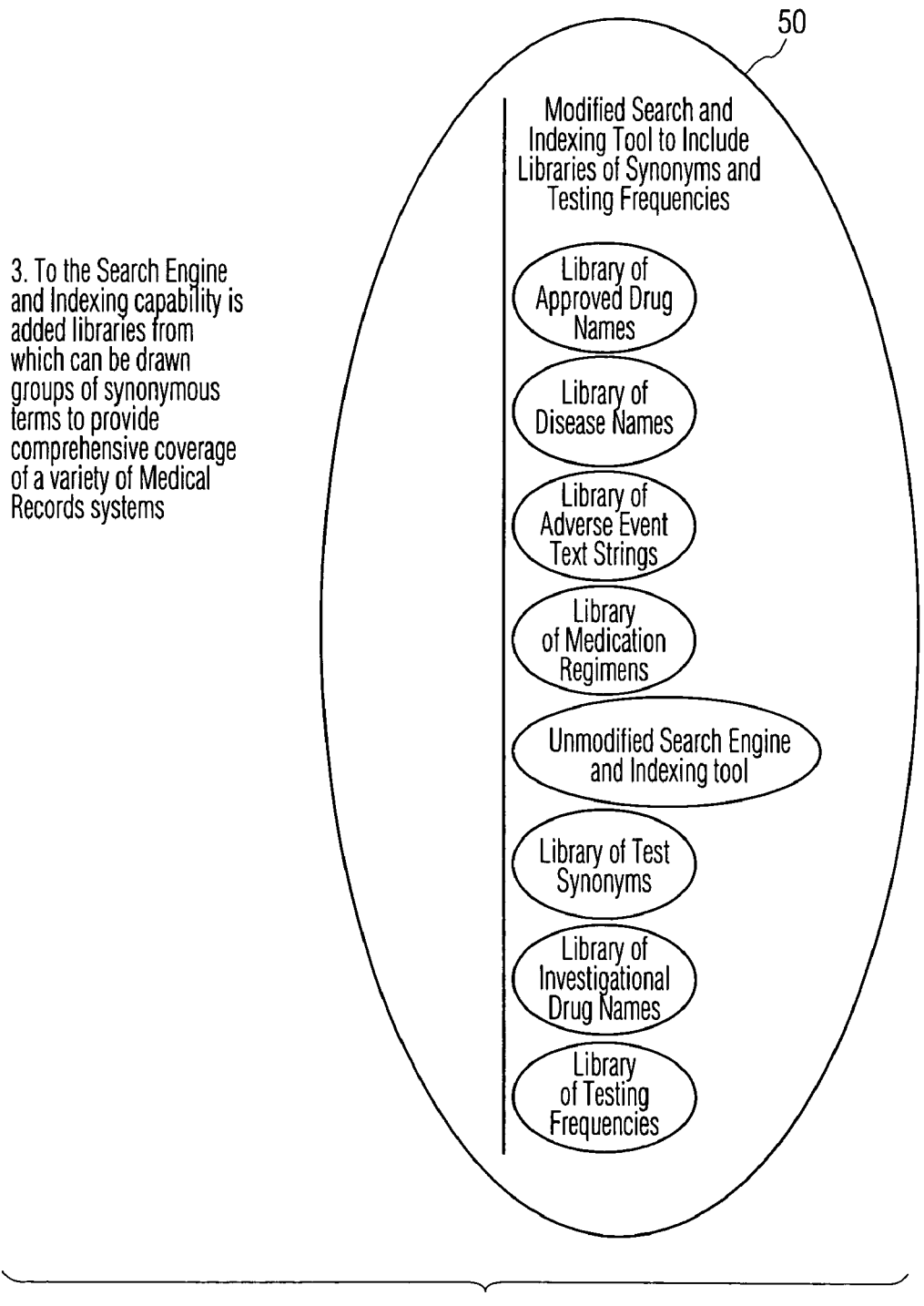
FIG. 4 diagrammatically shows the modifications that are made to utilize a Search Engine for one embodiment of the invention.
Figure 5:
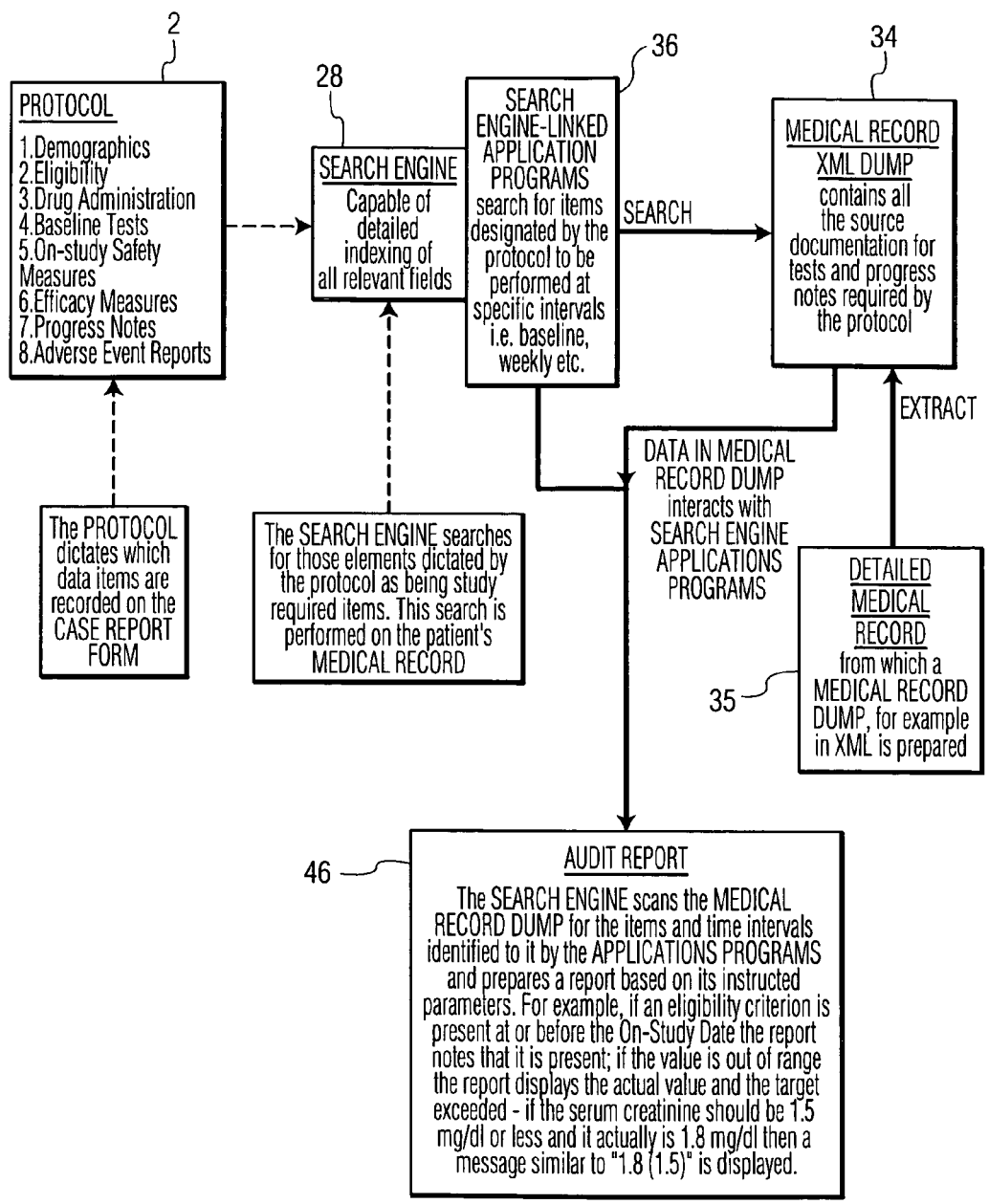
FIG. 5 is a flowchart showing another embodiment of the invention that provides an example of information that may appear in an Audit Report.

In FIG. 4, a string 50 of libraries of synonyms and testing frequencies are shown which the Audit Agency 14 may include, for example, in transforming the Search Engine in step 28 of FIG. 3. In this manner, the Search Engine is provided with a comprehensive coverage or library of a variety of Medical Records and systems. Also, in FIG. 5, a flowchart is shown for providing expanded details of steps 28, 36, and 34, the latter being shown to be an XML marked database of applicable Medical Records. The database of Medical Records formed in step 34, as shown, is extracted from detailed Medical Records shown in step 35, the latter including extracted data 26, as shown in FIG. 2 for each patient. Also, in step 46 of FIG. 5, examples are given of items that typically may appear in an Audit Report, as generated in step 46 of FIG. 3.

Figure 6:
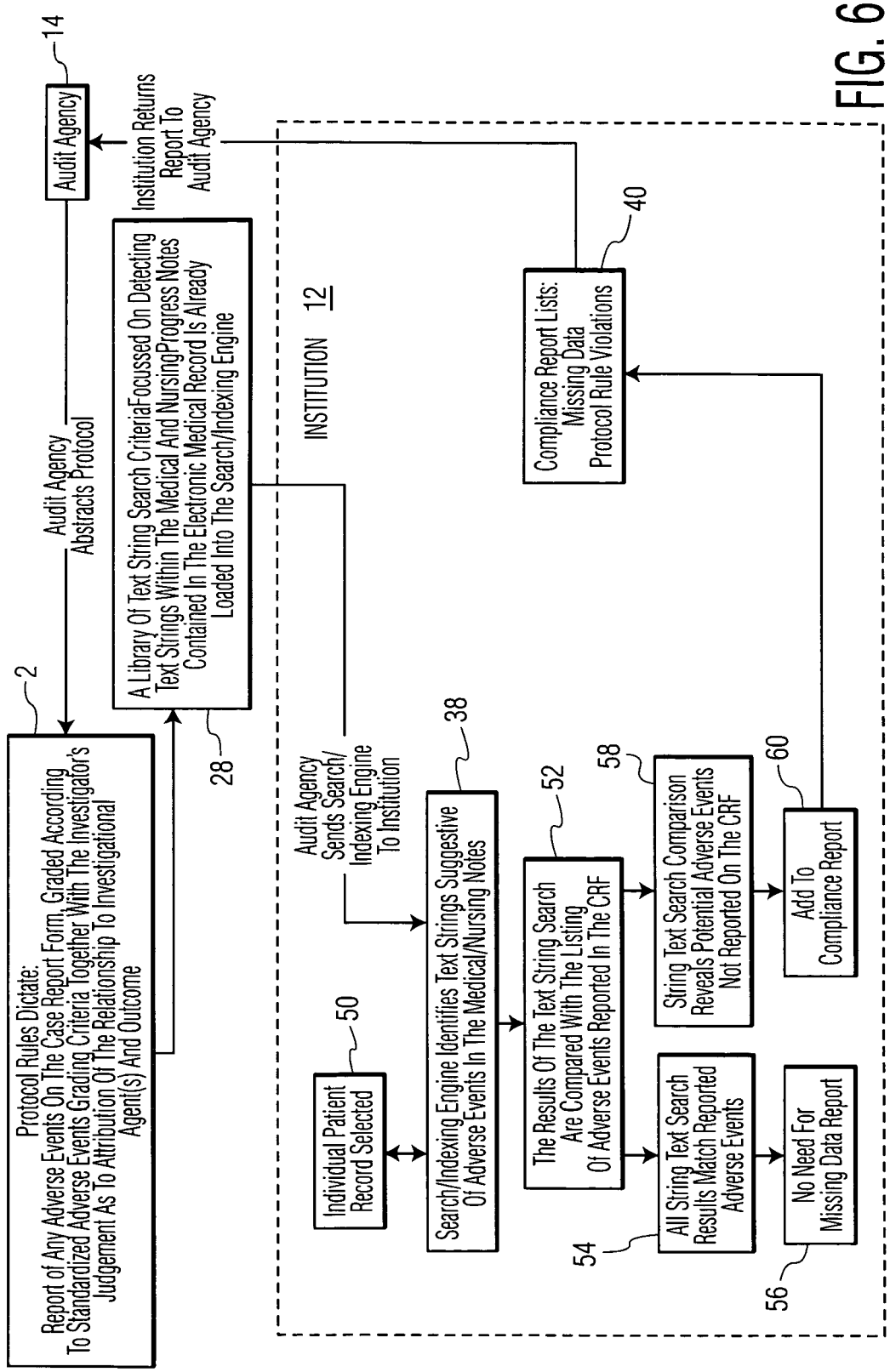
FIG. 6 is a flowchart showing greater details of various embodiments of the invention.

In FIG. 6, a flowchart is shown for other embodiments of the invention associated with the method and system of the flowchart of FIG. 3. As shown in the flowchart, Protocol rules of step 2 are indicated. The Audit Agency 14 transformation of a Search Engine in step 28 is further clarified. Also, as shown for the research Institution 12, individual patient records 50 are searched in step 38 by the Search Engine, with the records being obtained from the electronic patient record database of Institution 12. As indicated, in step 38 the Search and Indexing Engine identifies text strings suggestive of adverse events in medical/nursing notes contained within the Medical Records database. In step 52, the results of the text string search are compared with the listing of adverse events reported in the Case Report Form (CRF). If in step 54, results of step 52 show that the string of text search results match the printed adverse events, as indicated in step 56, there is no need for producing a Missing Data Report. However, as indicated in step 58, if the string text search comparison reveals potential adverse events that were not recorded on the CRF, then the adverse events are added to the Compliance Report in step 60. Following step 60, the Compliance Report is completed in step 40 to list missing data and Protocol rule violations. As previously shown in the flowchart of FIG. 3, in step 40, the Medical Research Institution 12 proceeds to step 42 for providing the Compliance Report to the Audit Agency 14.

Figure 7:
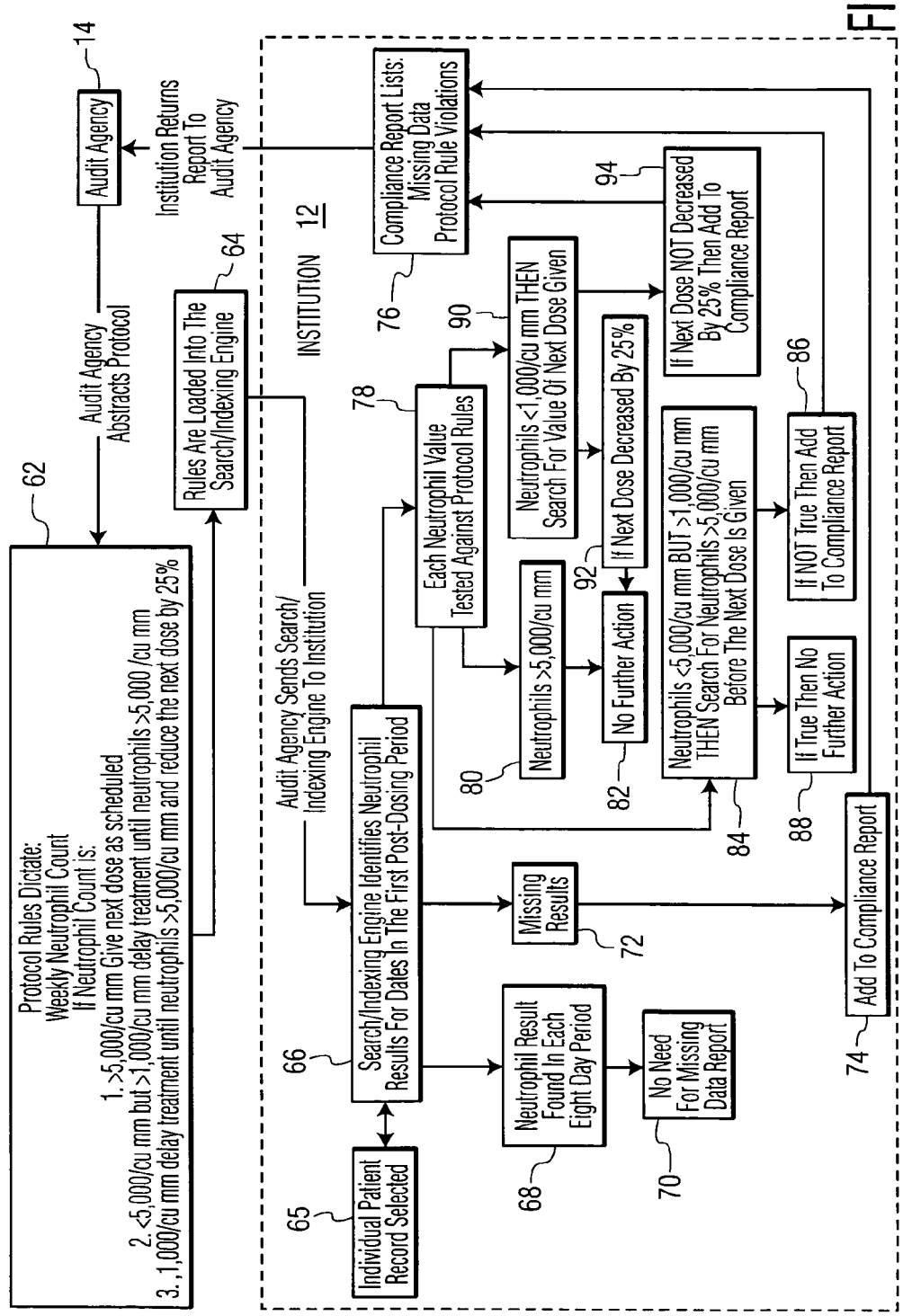
FIG. 7 is a flowchart providing an example of a particular Protocol rule, dictate or requirement as processed by the method and system for an embodiment of the invention.

In FIG. 7, a flowchart is shown for providing an example of one Protocol dictate, that is processed or audited by the Audit Agency 14. As indicated in step 62, the Protocol rules dictate for a weekly Neutrophil count is detailed, in this example. From step 62, step 64 is entered for loading the aforesaid Protocol Rules of step 62 into the Search/Indexing Engine. The Audit Agency 14 then sends the Search/Indexing Engine transformed in step 64 to the Medical Research Institute 12, which as previously indicated, then runs the Search Engine on the Electronic Patient Database previously prepared for auditing. In step 66, the Search/Indexing Engine identifies the Neutrophil results for dates in the first post-dosing period, as shown. These results are obtained from the individual patient records selected in step 65. As indicated in step 68, if a Neutrophil result is found in each eight-day period, then as indicated in step 70, there is no need for the Institution 12 to provide a missing data report. However, as indicated in step 72, if a Neutrophil result is missing, then step 74 is entered for adding the missing results to the previously mentioned Compliance Report. In step 76, all missing data and Protocol rule violations with respect to each individual patient record selected in step 65, is compiled into the Compliance Report. Also, note from step 66, step 78 is entered for testing each Neutrophil value against the Protocol rules, as shown in step 78. In the example given, if in step 80 it is determined from step 78 that the Neutrophil value is greater than 5,000/cu. mm., then as further indicated in step 82 no further action is required. If however, as shown from step 78 to step 84 it is found that the Neutrophil value did not meet the Protocol criteria, then in step 86 this is added to the Compliance Report operation of step 76. However, as shown in step 88, if in step 84 it is determined that indicated criteria is true or has been identified, then no further action is required. Also, proceeding from step 78, if it is determined in step 90 that the Neutrophil level for a given patient is as indicated, and the next dose as shown in step 92 is determined to have been decreased by 25%, then no further action is required, as indicated in step 82. However, if from step 90 it is determined as shown in step 94, that the next dose has not been decreased by 25%, then this deviation from the Protocol is added to the Compliance Report. Similar testing is required for each Protocol dictate, which may be more extensive than the examples previously given.

Figure 8:
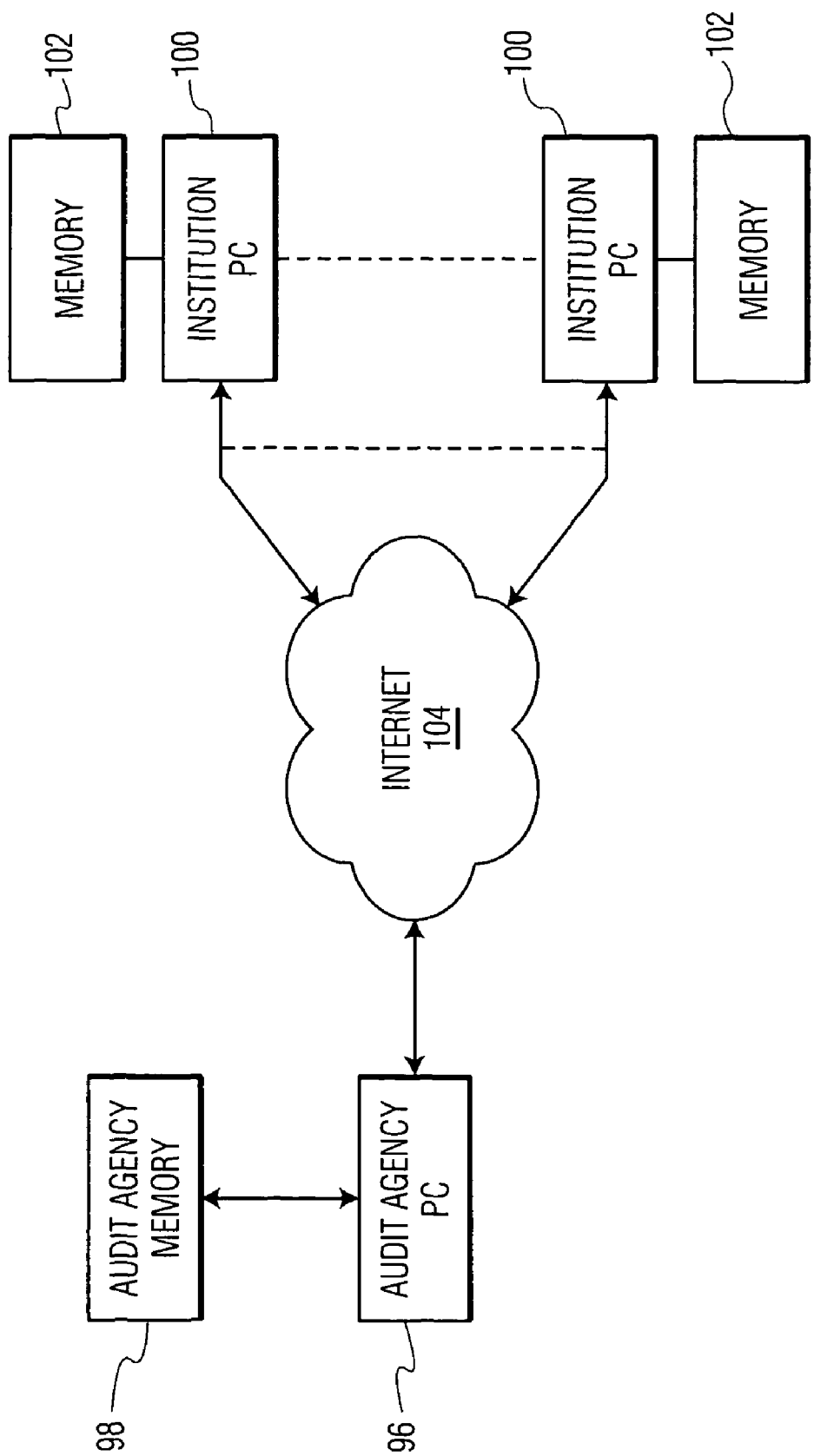
FIG. 8 is a block schematic diagram showing a simplified example of hardware requirements for carrying out the various embodiments of the invention between an Audit Agency and an Institution performing clinical testing of a new drug.

In FIG. 8, the general hardware requirements for carrying out the present system and method are shown. For this example, the Audit Agency 14 may have a personal computer 96 that is operable for storing and extracting information from a computer memory 98. A Medical Research Institution or Institutions conducting clinical studies which are to be audited by the Audit Agency 14, each may have a personal computer 100 which is typically connected to a large scale memory 102 that may be actually represented by a bank of memories depending upon the memory capacity required. As shown, in this example, the Audit Agency's personal computer 96 communicates with the various Medical Research Institution computers 100 via the Internet 104, in this example.

In summary of the method and system described above, and for providing further details, a suitable self-indexing Search Engine loaded with a library of appropriate synonyms used in commonly used field names, perhaps based, for example, on such standards as Health Level 7 (HL7) and Clinical Data Interchange Standards Consortium (CDISC) would be run against an XML dump from the stored data in the electronic patient records stored in memory 102. This stored data might be maintained with a database management system such as Oracle® or Focus® or a similar program in the live Institutional database, a clinical research database or an isolated copy of either. Probably an isolated copy of the patients enrolled on a specific Protocol would be preferred at the Institutional level to facilitate security and to prevent contamination of live data. The Search Engine, in addition to the described library would be primed with date windows to focus eligibility searches to within the Protocol-defined baseline data collection period. Matrices constructed on Protocol-required lab intervals would scan patient laboratory data for safety tests being obtained at the designated time points; latitude could be built in to these periods to allow for weekend- and holiday-dictated variations. Response assessment measures such as Computerized Tomography (CT) and Magnetic Resonance Imaging (MRI) evaluations could be targeted for the prescribed intervals and drug amount and timing surveyed for Protocol compliance. More complicated but possible safety/dosing relationships could be tested for.

The Search Engine would function in two ways, both with a discrete purpose. Firstly the Search Engine would return a report listing, for example, the eligibility-required items that it had failed to find. This report would continue to include missed evaluations on-study, missed or delayed response evaluations and the like. Secondly the Search Engine would report out actual values or result descriptions from its sweep where appropriate so that Protocol-dictated changes, if required, could be seen to have been made. At added levels of sophistication this process could be automated using derived rules of logic. For example, a tie could be made between degrees of neutropenia (see FIG. 7) and whether dose reduction rules were followed by looking at the grade of neutropenia and the subsequent values for investigational drug dosing. On the positive side, these reports would indicate whether a patient had full information to judge eligibility and whether these criteria were satisfied; whether dose reduction rules were followed; whether on study evaluations were obtained at the correct intervals; and whether objective evaluation criteria matched the stated best obtained response. On the negative side, it would be evident where insufficient information was gathered; where logical inconsistencies exist; and where stated responses are not supported by evaluation reports. Further, medical and nursing progress notes could be scanned against a library of synonyms to reveal areas requiring extra scrutiny to determine if there are unreported toxicities.

These reports would then be evaluated by the audit organization 14 and suspect records identified for subsequent detailed examination. This detailed examination would usually involve a comparison of the research record with source documents.

In pursuing a pilot study, for example, an Institution 12 would be selected which had the capability of making dumps directly from both their Medical Records database, and their clinical research record. In the first instance, the Institution 12 would be asked for several medical and clinical research records, from which the Institution 12 had removed patient identification. The Institution would be asked to prepare the data written two ways; firstly a copy of the raw medical and clinical research records for the selected patients and secondly, an appropriate dump of these records from the database. These records would be used as a test database to develop the library of search terms, and the code with which to scan the data for Protocol compliance.

There are various Libraries of Common Data Elements. CDISC (Clinical Data Interchange Standard Consortium) is the one preferred by the FDA. A popular clinical version is HL7 (Health Level 7 {formatting and Protocol standard}). A compilation of all agreed stands for Common Data Elements is maintained by CaBIG (Cancer Biomedical Informatics Grid).

A comprehensive classification system for adverse events—a massive dictionary—is known as MedRA (Medical Dictionary for Regulatory Activities). Many of the Clinical Information Systems use what are called PICK Lists; these can be lists of diagnoses, drug names, and so forth, where the operator selects the item from a hopefully comprehensive list of correctly spelled drug names for example. Dictionaries, many proprietary, exist for alternative ways of reporting adverse events including vast numbers of misspellings. One known dictionary contains over 40,000 items. This would form the basis for compiling the library of text string searches. One could characterize this by calling it the Clinical Trials Monitoring Service Adverse Event Dictionary.

The classic example of Search Engines is Google Desktop® desktop search software which in an appropriate version has the capability to search PDF's. The Google Desktop® desktop search software is believed applicable for use with the present invention.

Third generation languages are Focus® language, Oracle® language but there are many proprietary ways of handling Clinical Information that belong to large companies such as Siemens. Google Desktop® desktop search software has the capability of running application programs where logical functions can be applied to searches. These can be written in a number of languages of which XML is one. XML is the commonly used mark-up language. The present invention for computerized auditing of Medical Record databases containing legacy scanned documents or documents added by scanning from outside sources that may include, for example, hospital discharge summaries, central or other hospital laboratory reports, and pathology reports, can in the preferred embodiment to be best served by using a Search Engine that has the capability of indexing such scanned documents. As indicated, Google Desktop® desktop search software is such an indexing Search Engine identified for use with the present invention.

It is also believed that the following Search Engines can also be used in the present invention:
Albert® web;
Dieselpoint® Search;
Fast Data® Search;
interMedia® Search;
Isys:web® search engine:
MondoSearch® site search engine;
Oracle® Search;
Thunderstone Webinator® and Texis® RDBMS;
Ultraseek® search engine; and
YourAmigo® search engine.

Although various embodiments of the present invention have been shown and described, they are not meant to be limiting. Those of skill in the art may recognize certain modifications to these embodiments, which modifications are meant to be covered by the spirit and scope of the appended claims. For example, the present invention can also be used prospectively or retrospectively to extract data from a patient Medical Record database for research purposes. For example, a Pharmaceutical Company could transform a Search Engine to submit to an Institution for the latter's use in extracting trial data collected in accordance with the Company's Protocol without violation of Patient Privacy. The present invention can similarly be used to extract data related to epidemiologic studies.

What is claimed is:

1. A computerized method for permitting an institution running clinical trials on new drugs, which trials must be audited periodically by an outside Audit Agency, to prepare a Compliance Report independent of the outside Audit Agency, and to maintain Patient Privacy requirements mandated by HIPAA, relative to the Compliance Report to be provided to the outside Audit Agency, the method comprising:

outside Audit Agency steps including:
 using an outside Audit Agency computer programmed to transform a self-indexing Search Engine for independent use by said institution in preparing a Compliance Report for use by said outside Audit Agency to audit a clinical trial run by said Institution, the transformation steps including:
  constructing application programs containing Protocol requirements for a clinical trial to be audited, and necessary steps for permitting
 said Institution to run the transformed Search Engine on an Institution computer to prepare said Compliance Report;
  adding to the Search Engine said application programs; and
  storing the transformed Search Engine in an outside Audit Agency computer memory;
 using said outside Audit Agency computer to read said transformed Search Engine from said computer memory, and send the transformed Search Engine to said Institution;

said Institution steps including:
 programming an Institution computer to assemble individual electronic patient records from the clinical trial into a discrete database;
 programming said Institution computer to remove all personal information from each patient record;
 programming said Institution computer to assign a unique number or code to each patient record that permits only the Institution access to the patients' private information;
 programming said Institution computer to mark the patient records via a markup language to permit data in the patient records to be accessed by said transformed Search Engine;
 operating said Institution computer to receive and store in a memory the transformed Search Engine from said outside Audit Agency;
 using said Institution computer to read said transformed Search Engine from said memory, and run the transformed Search Engine independent of said outside Audit Agency to produce a Compliance Report detailing discrepancies relative to the Protocol dictated course of treatment for each said patient;
 storing the Compliance Report in said memory;
 using said Institution computer to retrieve said Compliance Report from said memory, and send sending the Compliance Report produced by said transformed Search Engine to said outside Audit Agency;

outside Audit Agency steps further including:
 receiving on said outside Audit Agency Computer the Compliance Report from said Institution;
 processing the Compliance Report on said outside Audit Agency computer to produce an Audit Report requesting comments, and if necessary, a corrective action plan, from the Institution;
 storing the Compliance Report, and the Audit Report in said outside Audit Agency memory; and
 using said outside Audit Agency computer to retrieve said Audit Report from memory, and send the Audit Report to the Institution.

2. The method of claim 1, wherein said Search Engine is a desktop search software.

3. The method of claim 1, wherein said markup language is Extensible Mark Up Language (XML).

4. The method of claim 1, wherein said step of transforming said Search Engine further includes the steps of
 adding a library of approved drug names;
 adding a library of disease names;
 adding a library of adverse event text strings;
 adding a library of medication regimens;
 adding a library of investigational drug names;
 adding a library of test synonyms; and
 adding a library of testing frequencies.

5. The method of claim 4, further including the steps of;
 said Institution providing in said discrete database a Case Report Form (CRF) containing the results and observations required by said Protocol for each patient in the clinical trial; and
 said outside Audit Agency programming said Search Engine to apply said library of adverse event text strings to detect text strings within medical and nursing progress notes contained in patient records in said discrete database, to identify text strings suggestive of adverse events in said notes;
 said outside Audit Agency further programming said Search Engine to compare the results of the text string search with a listing of adverse events reported in said CRF, and to add to the Compliance Report any potential adverse events not reported in the CRF.

6. The method of claim 4, wherein said outside Audit Agency further includes the step of insuring that the Protocol rules contained in said application programs include at least patient demographics, patient eligibility requirements, drug administration requirements, baseline test requirements, on-study safety measures to be followed, efficacy measurements, and adverse event report requirements.

7. The method of claim 6, further including the steps of:
 said Institution providing in said discrete database a Case Report Form (CRF) containing the results and observations required by said Protocol for each patient in the clinical trial; and
 said outside Audit Agency programming said Search Engine to apply said library of adverse event text strings to detect text strings within medical and nursing progress notes contained in patient records in said discrete database, to identify text strings suggestive of adverse events in said notes;
 said outside Audit Agency further programming said Search Engine to compare the results of the text string search with a listing of adverse events reported in said CRF, and to add to the Compliance Report any potential adverse events not reported in the CRF.

8. The method of claim 7, wherein said Search Engine is a desktop search software.

9. The method of claim 7, wherein said markup language is Extensible Mark Up Language (XML).

10. The method of claim 4, wherein said Institution further includes the step of insuring that the Medical Record for each patient stored in said discrete database contains all the source documentation for tests and progress notes required by the Protocol.

11. The method of claim 10, further including the steps of:
said Institution providing in said discrete database a Case Report Form (CRF) containing the results and observations required by said Protocol for each patient in the clinical trial; and
said outside Audit Agency programming said Search Engine to apply said library of adverse event text strings to detect text strings within medical and nursing progress notes contained in patient records in said discrete database, to identify text strings suggestive of adverse events in said notes;
said outside Audit Agency further programming said Search Engine to compare the results of the text string search with a listing of adverse events reported in said CRF, and to add to the Compliance Report any potential adverse events not reported in the CRF.

12. The method of claim 10, wherein said Search Engine is a desktop search software.

13. The method of claim 10, wherein said markup language is Extensible Mark Up Language (XML).

14. The method of claim 4, further including:
said outside Audit Agency further includes the step of insuring that the Protocol rules contained in said application programs include at least patient demographics, patient eligibility requirements, drug administration requirements, baseline test requirements, on-study safety measures to be followed, efficacy measurements, and adverse event report requirements; and
said Institution further includes the step of insuring that the Medical Record for each patient stored in said discrete database contains all the source documentation for tests and progress notes required by the Protocol.

15. The method of claim 14, further including the steps of:
said Institution providing in said discrete database a Case Report Form (CRF) containing the results and observations required by said Protocol for each patient in the clinical trial; and
said outside Audit Agency programming said Search Engine to apply said library of adverse event text strings to detect text strings within medical and nursing progress notes contained in patient records in said discrete database, to identify text strings suggestive of adverse events in said notes;
said outside Audit Agency further programming said Search Engine to compare the results of the text string search with a listing of adverse events reported in said CRF, and to add to the Compliance Report any potential adverse events not reported in the CRF.

16. The method of claim 14, wherein said Search Engine is a desktop search software.

17. The method of claim 14, wherein said step markup language is Extensible Mark Up Language (XML).

18. The method of claim 14, wherein:
said Search Engine is a desktop search software; and
said markup language is Extensible Mark Up Language (XML).

19. The method of claim 1, further comprising the step of:
communicating over the Internet between the outside Audit Agency and the Institution via personal computer systems of each.

20. The method of claim 1, wherein said outside Audit Agency further includes the step of insuring that the Protocol rules contained in said application programs include at least patient demographics, patient eligibility requirements, drug administration requirements, baseline test requirements, on-study safety measures to be followed, efficacy measurements, and adverse event report requirements.

21. The method of claim 1, wherein said Institution further includes the step of insuring that the Medical Record for each patient stored in said discrete database contains all the source documentation for tests and progress notes required by the Protocol.

22. The method of claim 1, wherein:
said Search Engine is a desktop search software; and
said markup language is Extensible Mark Up Language (XML).

23. A computerized method for permitting an Institution running clinical trials on new drugs, which trials must be audited periodically by an outside Audit Agency, to prepare a Compliance Report independent of the outside Audit Agency, and to maintain Patient Privacy requirements mandated by HIPAA, relative to the Compliance Report to be provided to said outside Audit Agency, the method comprising:
said outside Audit Agency steps including:
programming a computer to transform a self-indexing Search Engine by steps including:
constructing application programs containing the Institution's Protocol requirements for the clinical trial, and necessary steps for permitting said Institution to use a computer to prepare a Compliance Report;
adding to the Search Engine said application programs; and
sending the transformed Search Engine to said Institution;
said institution steps including:
using a computer to assemble individual electronic patient records from the clinical trial into a discrete database;
using a computer to remove all personal information from each patient record;
using a computer to assign a unique number or code to each patient record that permits only the Institution access to the patients' private information;
using a computer to mark the patient records via a markup language to permit data in the patient records to be accessed by said Search Engine;
storing the permitted patient data in a computer memory;
receiving on the computer the Search Engine from said outside Audit Agency;
running the Search Engine on a computer independent of said outside Audit Agency to produce a said Compliance Report detailing discrepancies relative to the Protocol dictated course of treatment for each said patient; and
sending via a computer the digitized Compliance Report produced by said Search Engine to said outside Audit Agency;
said outside Audit Agency steps further including:
receiving on a computer the Compliance Report from said Institution, and storing the Report in memory;
using a computer to read the Compliance Report from memory, and to produce an Audit Report requesting any necessary comments, and if necessary, a corrective action plan, from the Institution; and
using a computer to send the Audit Report to the Institution.

* * * * *